United States Patent [19]

Shaber et al.

[11] Patent Number: 5,624,916
[45] Date of Patent: Apr. 29, 1997

[54] FUNGICIDAL 1,2,4-TRIAZOLES

[75] Inventors: Steven H. Shaber, Horsham, Pa.; Luong T. Nguyen, Pinewood Garden, Singapore

[73] Assignee: Rohm and Haas Company, Philadelphia, Pa.

[21] Appl. No.: 489,416

[22] Filed: Jun. 12, 1995

Related U.S. Application Data

[62] Division of Ser. No. 269,874, Jun. 30, 1994, Pat. No. 5,462,931, which is a division of Ser. No. 904,230, Jun. 25, 1992, Pat. No. 5,358,939.

[51] Int. Cl.$^6$ ............... C07D 249/08; C07D 239/02; C07D 241/02; C07D 249/14; A01N 43/64
[52] U.S. Cl. ............... 514/63; 514/93; 514/255; 514/274; 514/340; 514/341; 514/383; 514/384; 544/315; 544/405; 546/272.4; 548/101; 548/110; 548/112; 548/262.2; 548/263.2; 548/264.2; 548/264.8; 548/265.2; 548/266.2; 548/266.8; 548/267.2; 548/267.8
[58] Field of Search ............... 548/267.8, 262.2, 548/101, 110, 112, 263.2, 263.8, 264.2, 266.2, 266.8, 267.2; 514/340, 383, 63, 93, 255, 274, 341, 384; 544/405, 315; 546/278

[56] References Cited

U.S. PATENT DOCUMENTS

| | | | |
|---|---|---|---|
| 4,278,800 | 7/1981 | Rentzea et al. | 548/267.8 |
| 4,315,764 | 2/1982 | Reiser et al. | 548/267.8 X |
| 4,319,911 | 3/1982 | Ammermann et al. | 548/267.8 X |
| 4,366,165 | 12/1982 | Miller et al. | 548/101 |
| 4,398,942 | 8/1983 | Ikari et al. | 71/92 |
| 4,411,687 | 10/1983 | Zeeh et al. | 548/101 |
| 4,466,974 | 8/1984 | Richardson et al. | 424/69 |
| 4,483,863 | 11/1984 | Richardson et al. | 424/269 |
| 4,554,286 | 11/1985 | Richardson et al. | 514/383 |
| 4,598,085 | 7/1986 | Heeres et al. | 514/383 |
| 4,622,335 | 11/1986 | Kramer et al. | 514/383 |
| 4,689,337 | 8/1987 | Bushell et al. | 514/383 |
| 4,868,196 | 9/1989 | Holmwood et al. | 548/267.8 X |
| 4,876,354 | 10/1989 | Siegal et al. | 548/267.8 X |
| 4,925,863 | 5/1990 | Bayles et al. | 514/383 |
| 4,980,367 | 12/1990 | Cuomo et al. | 514/383 |
| 4,987,144 | 1/1991 | Kanamaru et al. | 514/383 |
| 4,992,454 | 2/1991 | Richardson | 514/340 |
| 5,021,442 | 6/1991 | Colle et al. | 548/262.2 |
| 5,039,815 | 8/1991 | Seele et al. | 548/262.2 |
| 5,358,939 | 10/1994 | Shaber et al. | 514/63 |
| 5,364,870 | 11/1994 | Shaber et al. | 514/340 |
| 5,462,931 | 10/1995 | Shaber et al. | 514/63 |

FOREIGN PATENT DOCUMENTS

| | | | |
|---|---|---|---|
| 61798 | 10/1982 | European Pat. Off. | 548/267.8 |
| 46658 | 4/1983 | European Pat. Off. | 548/267.8 |
| 126430 | 11/1984 | European Pat. Off. | 548/267.8 |
| 52424 | 3/1985 | European Pat. Off. | 548/267.8 |
| 150152 | 8/1985 | European Pat. Off. | 548/267.8 |
| 3835742 | 5/1990 | European Pat. Off. | 548/267.8 |
| 234242 | 1/1992 | European Pat. Off. | 548/267.8 |
| 0470463 | 2/1992 | European Pat. Off. | 548/267.8 |
| 2921168 | 12/1980 | Germany | 548/267.8 |
| 2926096 | 1/1981 | Germany | 548/267.8 |
| 3221915 | 12/1983 | Germany | 548/267.8 |
| 3408127 | 9/1984 | Germany | 548/267.8 |
| 3813841 | 12/1988 | Germany | 548/266.6 |
| 2104065 | 3/1983 | United Kingdom | 548/267.8 |
| 214815 | 2/1985 | United Kingdom | 548/267.8 |

*Primary Examiner*—Floyd D. Higel
*Attorney, Agent, or Firm*—Joseph F. Leightner

[57] ABSTRACT

2-Aryl or 2-heterocyclyl-2, 2-disubstituted ethyl-1,2,4-triazoles have been shown to have fungicidal activity.

12 Claims, No Drawings

FUNGICIDAL 1,2,4-TRIAZOLES

This application is a divisional of U.S. Ser. No 08/269,874, filed on Jun. 30, 1994, which is now U.S. Pat. No. 5,462,931; which is a divisional of U.S. Ser. No. 07/904,230, filed Jun. 25, 1992, which is now U.S. Pat. No. 5,358,939.

FIELD OF THE INVENTION

This invention relates to (2-aryl or 2-heterocyclyl-2,2-disubstituted)-ethyl-1,2,4-triazoles, their enantiomorphs, acid addition salts and metal salt complexes, compositions containing these compounds and the use of these compounds as fungicides, particularly against phytopathogenic fungi.

DESCRIPTION OF THE RELATED ART

U.S. Pat. No. 4,366,165 discloses 1- and 4-arylcyanoalkyl-1,2,4-triazoles as fungicidal agents. The compounds of this disclosure are limited to those having a cyano group bonded to the beta carbon of the alkyl substituent on the triazole.

European Patent Publication No. 61,798 discloses 2-ethyltriazole derivatives having a phenyl substituent on the beta carbon of the ethyl group. All of the compounds of this disclosure also have a hydrogen atom attached to the beta carbon as well as a secondary or tertiary amino group.

European Patent Publication No. 52,424 discloses 2-ethyl substituted triazole compounds in which the beta carbon of the ethyl group has a chloro, cyano, or oxy substituent.

U.K. Patent Application No. GB 2104065A discloses microbial mandelic acid derivatives and mandelonitriles. These compounds are generally 2-ethyltriazoles in which the beta carbon of the ethyl group is substituted by an aromatic substituent, an oxy substituent, and a carboxyl or cyano group. All of the compounds of this disclosure require that at least one of the substituents on the beta carbon of the ethyl group be an oxy substituent.

U.S. Pat. No. 4,622,335 discloses fungicidal hydroxyethylazolyloxime derivatives. The compounds of this disclosure, in addition to having the oxime functionality on the asymmetric carbon, also all have a hydroxy group on the same carbon.

U.S. Pat. No. 4,598,085 discloses fungicidal 1-(2-aryl-2-R-ethyl)-1H-1,2,4-triazoles as fungicidal agents. The compounds of this disclosure all have a hydrogen atom on the beta carbon of the ethyl substituted triazole in addition to an optionally substituted phenyl group and lower alkyl, cycloalkyl, lower alkenyl, aryl methyl and aryl ethyl substituents.

German Patent Publication 3408127 discloses fungicidal N-(azolylethyl)carboxamides. The compounds of this disclosure reportedly have a carboxamide group attached to the beta carbon of the ethyl substituent of the triazole.

U.S. Pat. No. 4,398,942 discloses herbicidally active phenylacetonitriles. These compounds, while being substituted ethyltriazoles, have either a cyano or ethynyl group on the beta carbon of the ethyl substituent.

U.S. Pat. No. 4,411,687 discloses fungicidal azolyl glycol derivatives having ether or ester linkages at the beta carbon of 2-ethyltriazoles, along with a glycol substituent on the alpha carbon.

German Patent Publication 3221915 discloses fungicidal esters having chloro substitutents on the alpha carbon of 2-ethyltriazoles and alkyl esters on the beta carbon.

European Patent Publication 234,242 discloses fungicidal 2-ethyltriazoles with fluoroalkyloxy substituents on the beta carbon of the ethyl chain.

European Patent Publication No. 46,658 discloses bistriazolyl ketones in which the bridging ethylene has a lower alkyl carbonyl substituent.

SUMMARY OF THE INVENTION

This invention relates to novel (2-aryl or 2-heterocyclyl-2,2-disubstituted)ethyl-1,2,4-triazoles, the enantiomorphs, acid addition salts and metal salt complexes thereof, and their use as highly active broad-spectrum systemic fungicides.

This invention relates to compounds of the formula:

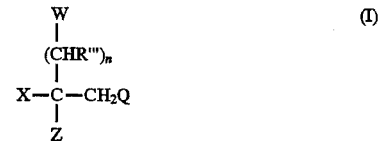

wherein X is optionally substituted aryl or optionally substituted heterocydyl such as pyridyl, pyrimidinyl, pyrazinyl, thienyl furyl and the like;

Q is optionally substituted 1-(1,2,4-triazolyl) or 4-(1,2,4-triazolyl);

Z is alkyl, haloalkyl, alkenyl, haloalkenyl, alkynyl, cydoalkyl, cycloalkenyl, cycloalkylalkyl, aryl, aralkyl, heterocyclyl or heterocyclylalkyl, provided X and Z are not both heterocyclyl groups;

W is an ether, ester, amine, amide, sulfonate, urethane, dialkylphosphate or trialkylsiloxy, all optionally substituted, or is halo or hydroxy;

R''' is hydrogen or alkyl;

n is an integer from one to six; and the agronomically acceptable enantiomorphs, acid addition salts and metal salt complexes thereof.

DETAILED DESCRIPTION OF THE INVENTION

In particular, this invention relates to compounds of the formula:

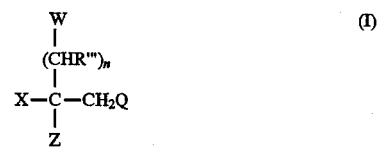

wherein X is optionally subsuted aryl such as phenyl, naphthyl, and the like or optionally substituted heterocyclyl such as pyridyl, pyrimidinyl, pyrazinyl, thienyl or furyl;

Q is optionally substituted 1-(1,2,4,-triazolyl) or 4-(1,2, 4-triazolyl);

Z is $(C_1-C_{12})$alkyl, halo$(C_1-C_{12})$alkyl, $(C_2-C_8)$alkenyl, halo$(C_2-C_8)$alkenyl, $(C_2-C_8)$alkynyl, $(C_3-C_8)$cydoalkyl, $(C_5-C_8)$cycloalkenyl, cycloalkylalkyl, aryl, aralkyl, heterocyclyl or heterocyclylalkyl, provided X and Z are not both heterocyclyl groups;

W is —OR, —OCOR'', —OCOY, —OCOR'Y, —OCOR'OR'', —OR'OCOR'', —OR'OR, —NH$_2$, —NHCOR, —NHCOR'Y, —NHCOY, —OCONHY, —OSO$_2$A, —OSiA$_3$, —OPO(OA)$_2$ or halo; wherein A is $(C_2-C_6)$alkyl, R is $(C_1-C_{12})$alkyl, X, Y-alkyl, $(C_3-C_8)$alkenyl, $(C_3-C_8)$alkynyl, $(C_3-C_8)$cycloalkyl, cyanoalkyl or epoxyalkyl, all optionally halogenated, or is hydrogen, provided that when Z is methyl, R is not haloalkyl;

R' is (—CH(CH$_3$)—)$_p$(—CH$_2$—)$_m$ or (—CH$_2$—)$_s$ CH=CH(—CH$_2$—)$_r$;

m is an integer from 0 to 6;

p is 0 or 1, provided m and p are not both 0;

s and t are each independently integers of from 0 to 3;

R" is phenyl, $(C_1-C_6)$alkyl, $(C_2-C_4)$alkenyl or $(C_1-C_2)$-trialkylsilyl$(C_1-C_4)$alkyl, all optionally halogenated, or is hydrogen;

R'" is hydrogen or $(C_1-C_6)$alkyl;

n is an integer from 1 to 6;

Y is phenyl, naphthyl, piperidinyl, triazolyl, pyrazinyl, pyrimidinyl, phthalimido, morpholinyl, pyridyl, thienyl, furyl or cycloalkyl, all optionally substituted; and the agronomically acceptable enantiomorphs, acid addition salts and metal salt complexes thereof.

The term "aryl" means an aromatic ring structure of from 6 to 10 carbon atoms, preferably a phenyl or a naphthyl group. The aryl group may be optionally substituted with up to three substituents, preferably with up to two substituents, selected from the group consisting of hydroxy, halo, acetoxy, trihalomethyl, $(C_1-C_4)$alkyl, $(C_1-C_4)$ alkoxy, $(C_1-C_4)$ alkylthio, $(C_1-C_4)$alkylsulfinyl, $(C_1-C_4)$alkylsulfonyl, $(C_1-C_4)$-alkoxy$(C_1-C_4)$alkoxy, $(C_1-C_4)$alkylcarbonyl, $(C_2-C_8)$alkenyl, $(C_2-C_4)$-alkenyloxy, $(C_2-C_8)$alkynyl, $(C_2-C_4)$alkynyloxy, phenyl, phenyl monosubstituted with halo, alkyl or alkoxy, phenoxy and phenoxy monosubstituted with halo, alkyl or alkoxy. Typical aryl groups include, but are not limited to, phenyl, naphthyl, 4-chlorophenyl, 4-fluorophenyl, 2-methoxyphenyl, 4-phenylphenyl, 4-(4'-chlorophenyl)phenyl, 4-phenoxyphenyl, 2-chloro-4-(4'-chlorophenoxy)phenyl, 2,4-dibromophenyl, 3,5-difluorophenyl, 2,4,6-trichlorophenyl, 2,3,4-tribromophenyl, 3,4-dichlorophenyl, 2-chloro-4-iodophenyl, 3-chloro-4-nitrophenyl, 3,4,5-trimethylphenyl, 2-chloronaphthyl, 2,4-dimethoxyphenyl, 4-(trifluoromethyl)phenyl, 3,5-bis(methylthio)phenyl, 2-cyano-5-methylphenyl, 2,4-bis(methylsulfinyl)phenyl, 2,4-bis(methylsulfonyl)phenyl, 2,4-diiodonaphthyl and 2-iodo-4-methylphenyl.

The term "heterocyclyl" means 5 and 6 membered rings having up to three embedded atoms selected independently from nitrogen, oxygen and sulfur, and includes, but is not limited to, furan, thiophene, triazole, imidazole, pyridine, pyrimidine, pyrazole, oxazole, piperazine and morpholine, all optionally substituted with up to two substituents independently selected from alkyl and halo.

Unless otherwise defined, the term "alkyl" includes both branched and straight chained alkyl groups of from 1 to 12 carbon atoms. Typical alkyl groups are methyl, ethyl, n-propyl, isopropyl, n-butyl, sec-butyl, isobutyl, t-butyl, n-pentyl, neopentyl, isopentyl, hexyl, heptyl, isooctyl, nonyl, decyl, isodecyl, undecyl, dodecyl and the like. The alkyl groups may be halogenated.

The term "alkylenyl" refers to a bivalent alkyl group in which two free bonds can be on the same carbon or different carbons.

The term "aralkyl" defines a group wherein the alkyl chain is from 1 to 4 carbon atoms, branched or straight chained, and the aryl portion of the group is defined as above. Typical aralkyl groups include, but are not limited to, 2,4-dichlorobenzyl, 2,4-dibromobenzyl, 2,4,6-trichlorobenzyl, 3,5-dimethoxyphenethyl, 2,5-bis(methylsulfonyl)phenethyl, 2,4,5-trimethylphenylbutyl, 2,4-dicyanonaphthylmethyl, 2,4-dibromonaphthylbutyl, 4-chlorophenethyl, 4-fluorophenethyl, 4-(trifluoromethyl)phenethyl and the like.

The terms "alkenyl" and "alkynyl" include branched and straight chain hydrocarbons of from 2 to 8 carbon atoms having at least one unsaturated bond. These substituents may be halogenated.

The term "alkenylenyl" refers to a bivalent alkenyl group in which the two free bonds are on different carbons.

In the definition of Q, the term "optionally substituted 1-(1,2,4-triazolyl) or 4-(1,2,4-triazolyl)" includes unsubstituted 1- and 4-(1,2,4-triazolyl) and 1- and 4-(1,2,4-triazolyl) substituted with up to two substituents selected from the group consisting of halo, $(C_1-C_4)$alkyl, nitro, cyano, mercapto and $(C_1-C_8)$alkylmercapto.

As used herein and in the appended claims, the symbol "OCOR" refers to a group in which the carbon of the carbonyl moiety is bonded to R; the symbol "COOR" refers to a group in which the non-carbonyl oxygen is bonded to the R group.

The acids which can be utilized in making the acid addition salts of the present invention include hydrochloric, hydrobromic, nitric, sulfuric, phosphoric, hydriodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complexes of the formula

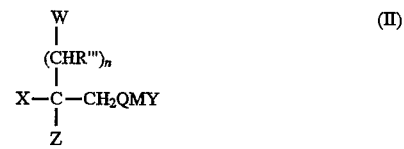

(II)

wherein X, Z, Q, R'" and W are as defined in Formula (I) above, M is a cation selected from Group IIA, IVA, IB, IIB, VIB, VIIB and VIII of the Periodic Table and Y is an anionic counterion selected to neutralize the charge of the cation M.

Typical cations encompassed by this invention are magnesium, manganese, copper, nickel, zinc, iron, cobalt, calcium, tin, cadmium, mercury, chromium, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartrate, realate, maleate, fumarate, p-toluenesulfonate, methanesulfonate, mono- or di$(C_1-C_4)$alkyldithiocarbamate, $(C_1-C_4)$alkylenebisdithiocarbamate and the like.

A preferred embodiment of this invention is the compounds, enantiomorphs, salts and complexes of Formulas (I) and (II) wherein X is phenyl optionally substituted with up to three substituents, preferably with up to two substituents, selected from halo, preferably chloro, trihalomethyl, preferably trifluoromethyl, $(C_1-C_4)$alkyl, $(C_1-C_4)$alkoxy, $(C_1-C_4)$alkylthio, phenoxy, monohalophenoxy and phenyl; Z is $(C_1-C_8)$alkyl, halo$(C_1-C_{12})$alkyl, $(C_5-C_7)$cycloalkyl, $(C_3-C_7)$cycloalkyl$(C_1-C_5)$alkyl, $(C_2-C_8)$alkenyl, halo$(C_2-C_8)$alkenyl, $(C_5-C_6)$cycloalkenyl, $(C_2-C_4)$alkynyl, phenyl, benzyl, phenethyl and phenyl, benzyl or phenethyl, the aromatic ring being substituted with up to two halo substituents or trihalomethyl, R'" is H and n is 1 provided that when Z is methyl, R is not haloalkyl, and Q is 1-(1,2,4-triazolyl)).

A more preferred embodiment of this invention is the compounds, enantiomorphs, salts and complexes of Formulas (I) and (II) wherein X is phenyl, optionally substituted at the 4-position with chloro, bromo, fluoro, hydroxy, acetoxy, methoxy or ethoxy or trifluoromethyl; Z is $(C_1-C_6)$alkyl, $(C_5-C_6)$cycloalkyl, preferably ethyl or n-butyl phenyl, benzyl, phenethyl or monochloro substituted phenyl, benzyl or phenethyl, such as 4-chlorophenyl, 2-chlorobenzyl, 4-chlorophenethyl, R is $(C_1-C_4)$alkyl, $(C_1-C_4)$haloalkyl, $(C_3-C_4)$alkenyl, $(C_3-C_4)$alkynyl, or optionally halo substituted phenyl, benzyl or phenethyl and R" is ($C_1$-$C_4$)alkyl or phenyl provided that when X is phenyl, R is not haloalkyl and Q is 1-(1,2,4-triazolyl).

The compounds described and claimed herein were synthesized starting from the arylcyanoalkyl-1,2,4-triazoles of Miller, U.S. Pat. No. 4,366,165, the disclosure of which is herein incorporated by reference. The general steps are:
A. Hydrolysis of nitrile to acid;
B. Hydrolysis of nitrile to amide;
C. Hydrolysis of amide to acid;
D. Reduction of acid to hydroxymethylene;
E. Reduction of nitrile to aminomethylene;
F. Acylation of hydroxymethylene to acylmethylene;
G. Formation of sulfonates;
H. Acylation of aminomethylene to amidomethylene;
I. Etherification of hydroxymethylene to alkoxymethylene;
J. Grignard addition to nitrile to form a carbonyl followed by reduction.

These procedures apply to (2-aryl)ethyl-1,2,4-triazoles in which the aryl group is either substituted or unsubstituted. The methods employed are well known and can be found in any standard treatise on synthetic chemistry, such as March, Advanced Organic Chemistry—Reactions, Mechanism and Structure, 3rd Edition, John Wiley & Sons, 1985, (hereinafter "March") the disclosure of which is herein incorporated by reference. The following reaction schematic outlines the cascade. In this scheme, X, Q, Z, R'" and A are as defined for Formula I and G may be R or R' as defined for Formula I.

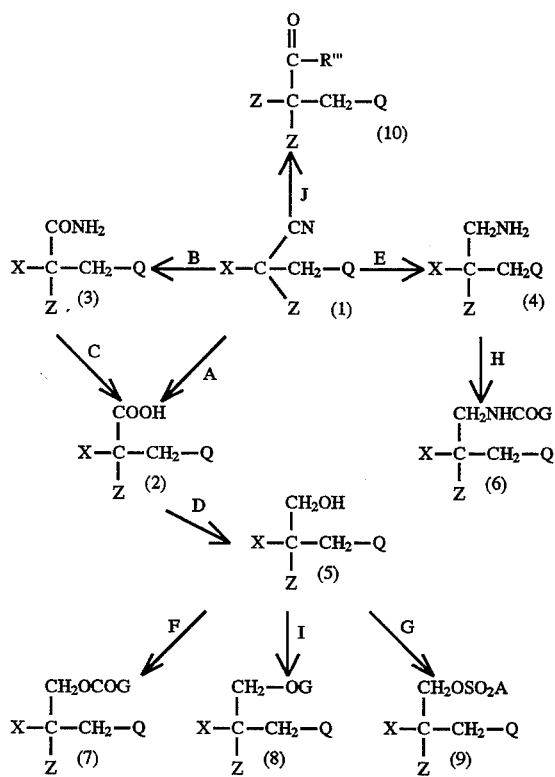

Scheme 1

Step A: Hydrolysis of Nitrile to Acid (March, p. 788)

The hydrolysis of a nitrile derivative (1) to a carboxylic acid (2) is performed under strongly acidic conditions using acids such as concentrated hydrochloric, 50–96% sulfuric, 48% hydrobromic and concentrated nitric acids; preferably, the hydrolysis is conducted at a temperature of about 100°–140° C. with 48% hydrobromic acid or concentrated hydrochloric acid for up to four days.

Step B: Hydrolysis of Nitrile to Amide (March, p. 788)

The hydrolysis of a nitrile (1) to an amide (3) is conveniently effected with either a strong acid, such as used in Step A, or a strong base. When an acid is used, the hydrolysis is preferably conducted 95% sulfuric acid at a temperature of about 80°–130° C., more preferably at a temperature of about 90°–110° C. for up to seven days. Strongly basic conditions may be obtained by selecting a base such as concentrated sodium, potassium or lithium hydroxide. In addition to water, the hydrolysis may also be run in the presence of another solvent, for example a dipolar aprotic solvent such as dimethyl sulfoxide. Preferably, the hydrolysis is conducted with concentrated sodium hydroxide for about 1 to 3 hours. Generally, it is conducted at a temperature of about 80°–130° C., more preferably about 90°–110° C.

Step C: Hydrolysis of Amide to Acid (March, p. 338)

The amides (3) can be hydrolyzed to the corresponding carboxylic acids (2) directly using a strong acid such as those of Step A or to the salt of a carboxylic acid using a strong base such as those of Step B. Strong acids are preferred, preferably about 45–95% sulfuric or about 48% hydrobromic acid. The amide is reacted with the appropriate acid or base at a temperature of about 80°–160° C. and more preferably about 80°–130° C. This procedure is preferred for ortho-substituted phenyl derivatives.

Step D: Reduction of Acid to Hydroxymethylene (March, p. 1099)

Hydroxymethylene (primary alcohol) derivatives (5) may be conveniently prepared by reduction of the carboxylic acid (2) or ester by a metal hydride, preferably lithium aluminum hydride, in an ether solvent such as dry tetrahydrofuran (THF) or diethyl ether at a temperature of from about 0° C. to about ambient room temperature, preferably 5°–20° C., for periods of up to about 24 hours.

Step E: Reduction of Nitrile to Aminomethtylene (March, p. 815)

Aminomethylene (primary amine) derivatives (4) may be conveniently prepared by reduction of the nitrile (1) with a metal hydride, preferably lithium aluminum hydride, in an ether solvent such as dry THF or diethyl ether at a temperature of from about 0° C. to about ambient room temperature for up to about 24 hours, usually from about 1–6 hours.

Step F: Acylation of Hydroxymethylene to Acylmethylene (March, pp. 346–348)

Acylmethylene derivatives (7) can be prepared by alcoholysis of acyl halides or anhydrides or esterification of acids with hydroxymethylene derivatives (5). An acid chloride can be added to the hydroxymethylene compound in an appropriate solvent such as THF in the presence of a base, such as triethylamine or pyridine. Reaction temperatures from about ambient room temperature to about 60° C. may be employed with reaction times up to about 24 hours.

Step G: Formation of Sulfonates (March, p. 358)

Sulfonates (9) can be prepared from hydroxymethylene compounds (5) and alkyl- or arylsulfonyl chlorides, such as methane-, ethane-, benzene- or toluenesulfonyl chloride. The hydroxymethylene in a solvent, such as methylene chloride or toluene, is reacted with the sulfonyl chloride in the presence of a base, such as triethylamine or pyridine. Reaction temperatures are from about 0°–50° C., preferably about 10°–30 ° C. and reaction times are up to about 24 hours.

Step H: Acylation of Aminomethylene to Amidomethylene (March, p. 370)

The synthesis of amidomethylenes (N-substituted amides) (6) can be carried out by the acylation of the aminomethylenes (4) with an acyl halide, an acid anhydride or a carboxylic ester. Preferably an acyl halide is reacted with the aminomethylene compound in the presence of a non-polar solvent, such as methylene chloride or toluene, at about 0°–50° C., preferably 10°–35° C., for up to about 24 hours. Alternatively, an acid anhydride, such as acetic anhydride, may reacted with the aminomethylene compound in the presence of a base, such as pyridine, at temperatures from about 0°–50° C. and more preferably from about 15°–35° C. for up to about 12 hours.

Step I: Etherification of Hydroxymethylene to Alkoxymethylene (March, p. 342)

Alkoxymethylenes (ethers) (8) can be prepared by first generating an alkali metal salt of the hydroxymethylene (alcohol) compound (5) with a strong base such as an alkali metal hydride, preferably sodium hydride, in a dipolar aprotic solvent, such as DMF or tetrahydrofuran, at a temperature from about 0°–50° C., preferably about 10°–30° C., for up to about 6 hours. An alkyl, aralkyl, alkenylalkyl or, alkynylalkyl halide, preferably a bromide or iodide, is added and the reaction run at about 0°–50° C., preferably 10°–30° C., for up to about 24 hours.

Alternatively, the sulfonates (9) or halogen derivative (W=halogen) can be reacted with an alkoxide or phenoxide (generated from the alcohol or phenol and a base such as sodium hydride in THF) in a suitable solvent such as THF from about 0°–50° C., preferably from about 10°–30° C., for up to 24 hours.

Step J: Grignard Addition to Nitrile Followed by Reduction (March, pp. 828, 1093)

When R''' is not H, in Formula I, the hydroxymethylene derivative (secondary alcohol) may be conveniently prepared by reaction of the nitrile (1) with on organometallic reagent such as an alkyllithium or, more preferably, a Grignard reagent, R''' MgX in ether or THF at reflux. The resulting ketone (10) can be reduced, Step D, to provide the secondary alcohol which can be derivatized as in steps F, G, and I.

When n is 2, in Formula 1, the derivatives may be prepared from (9) by reaction with an alkali metal cyanide, such as potassium or sodium cyanide in DMF or more preferably DMSO from 80°–130° C., preferably 90°–120° C. for up to about 24 hours. The cyanomethylene analog of (1) can then be reacted as in Scheme 1. These transformations can be repeated to provide homologs where n is greater than 2.

The acid addition salts of the 1,2,4-triazoles of this invention can be prepared by standard techniques well-known in the art. For example, the 1,2,4-triazole of Formula (I) can be dissolved in an appropriate solvent such as diethyl ether, tetrahydrofuran, ethanol, methanol, and the like or combinations thereof, and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above 1,2,4-triazoles can be prepared by adding dropwise, with stirring, a stoichiometric amount of a metal salt dissolved in an appropriate solvent or combination of solvents. The reaction mixture is briefly stirred and the solvent is removed under reduced pressure to give the metal salt complex of the 1,2,4-triazoles of Formula (II).

The metal salt complexes can also be prepared by mixing stoichiometric or excess amounts of the metal salt and a triazole of Formula (I) in the desired amount of solvent containing the appropriate adjuvants just prior to spraying the plants. Adjuvants that may be included in this in-situ preparation may be detergents, emulsifiers, wetting agents, spreading agents, dispersing agents, stickers, adhesives, and the like which are used in agricultural applications.

Solvents that can be utilized in these procedures include any polar solvent for example, water, methanol, ethanol, isopropanol or ethylene glycol and any aprotic dipolar solvent for example, dimethyl sulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Anions such as chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

Metal-containing fungicides can also act as safening agents when used in place of metal salts. Typical metal-containing fungicides that can be utilized in these procedures are: (1) dithiocarbamates and derivatives such as ferbam, ziram, maneb, mancozeb, and zineb; (b) copper-based fungicides such as cuprous oxide, copper oxychloride, copper naphthenate, and Bordeaux mixture; and (c) miscellaneous fungicides such as phenylmercuric acetate, N-ethylmercuri-1,2,3,6-tetrahydro-3,6-endomethano-3,4,5,6,7,7-hexachlorophthalimide, phenylmercuric monoethanol ammonium lactate, nickel-containing compounds and calcium cyanamide.

The compounds of this invention possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

EXAMPLE A (Procedure A)

2-(4-chlorophenyl)-2-[(1,2,4-triazol-1-yl)methyl] hexanoic Acid

To a 500 milliliter (mL) flask was charged 60.0 grams (g) (0.208 mole) of alpha-n-butyl-alpha-(4-chlorophenyl)-1H-1,2,4-triazole-1-propanenitrile followed by 200 mL of 48% hydrobromic acid. The mixture was stirred at reflux for 96 hours after which gas liquid chromatography (GLC) indicated disappearance of the starting material. The reaction was diluted with ethyl ether and extracted with water until pH neutral. The ether was extracted with sufficient 10% sodium hydroxide to pH 14 followed by separation with 35% hydrochloric acid at which time a white solid precipitate formed. The solid was collected by filtration and washed with water until the aqueous rinse was neutral. The product was dried under vacuum and gave 49.0 g (76.5% yield) of a white solid, melting point 169°–171° C.

EXAMPLE B-1 (Procedure B)

2-(2,4-dichlorophenyl)-2-[(1,2,4-triazol-1-yl)methyl] hexanoamide

To a 250 mL flask was charged 38.16 g (0.119 mole) of alpha-n-butyl-alpha-(2,4-dichlorophenyl)-1H-1,2,4-triazole-1-propanenitrile followed by 100 mL (0.63 moles) of 48% hydrobromic acid. The mixture was stirred at reflux for 48 hours after which GLC indicated disappearance of the starting material. The reaction was cooled to room temperature and neutralized with concentrated ammonium hydroxide (100 mL) to pH 8 and then to neutral pH with concentrated hydrochloric acid. A gummy oil formed which was diluted with 200 mL of ethyl acetate. The organic phase (3×200 mL ethyl acetate) was washed with 100 mL of water (3×). The organic phase was dried and concentrated to give a tan solid which was recrystallized from ethyl ether. The product was filtered and gave 22.78 g (56.3% yield) of a solid, melting point 170°–172° C.

EXAMPLE B-2 (Procedure B)

2-(4-chlorophenyl)-2-[(1,2,4-triazol-1-yl)methyl] hexanamide

To a 500 mL flask was charged 75.0 g (0.24 mole) of alpha-n-butyl-alpha-(4-chlorophenyl)-1H-1,2,4-triazole-1-propanenitrile followed by 300 mL of 95% sulfuric acid. The mixture was stirred at 90° C. for 7 days after which the mixture was cooled to room temperature, diluted with ice and neutralized with ammonium hydroxide until basic (pH 8). The product was extracted with ethylene dichloride then washed with water and dried over magnesium sulfate. The solvent was concentrated and gave 45 g (56.5% yield) of a solid melting point 197°–199° C.

EXAMPLE B-3 (Procedure B)

2-(4-chlorophenyl)-2-[(1,2,4-triazol-1-yl)methyl] butyramide

To a 500 mL flask was charged 100.0 g (0.38 mole) of alpha-(4-chlorophenyl)-alpha-ethyl-1H-1,2,4-triazole-1-propanenitrile and 100 mL of dimethyl sulfoxide. To the stirring solution was added 100 g (1.25 mole) of 50% sodium hydroxide. The reaction mixture was heated at 100° C. for 1 hour after which GLC indicated the starting material was consumed. The reaction was poured into water and extracted with ethyl acetate. After washing with brine, the organic phase was dried over magnesium sulfate and concentrated under vacuum without heating. Removal of the solvent gave a foamy glassy solid which was triturated with hexane, filtered and gave 97 g (91% yield) of a white solid, melting point 139°–140° C.

EXAMPLE B4 (Procedure B)

2-(2,4-dichlorophenyl)-2-[(1,2,4-triazol-1-yl)methyl] butyramide

To a 1 liter flask was charged 206.5 g (0.7 mole) of alpha-(2,4-dichlorophenyl)-alpha-ethyl-1H-1,2,4-triazole-1-propanenitrile and 500 mL of dimethyl sulfoxide and 200 mL of water. To the stirring solution was added 67.2 g (0.84 moles) of 50% sodium hydroxide. The reaction mixture was heated at 91° C. (steam bath) for 3 hours after which GLC indicated the starting material was consumed. The reaction was cooled to 30° C. then poured into water and extracted with ethyl acetate. After drying, the ethyl acetate was treated with charcoal and filtered through Celite®. Removal of the solvent gave a foamy oil which was stirred and diluted with ethyl acetate then treated with hexane until cloudy. Within 1 hour a solid formed which was cooled at 0° C. The product was filtered and washed with an ether and hexane mixture, then dried and provided 172 g (79% yield) of a white solid, melting point 164°–165° C.

EXAMPLE B-5 (Procedure B)

4-(4-chlorophenyl)-2-phenyl-2-[(1,2,4-triazol-1-yl) methyl]butyramide

To a 2 L flask was charged 320.0 g (0.95 mole) of alpha-(2-4-chlorophenyl)-ethyl)-alpha-phenyl-1H-1,2,4-triazole-1-propanenitrile, 685 mL dimethyl sulfoxide and 275 mL of water. To the stirring solution was added 91.3 g(1.14 moles) of 50% sodium hydroxide. The reaction mixture was heated at 95° C. for 3 hours after which GLC indicated the starting material was consumed. The reaction was cooled to 20° C. and the mixture was transferred to a 5 liter separatory funnel to which was added 1000 mL ethyl acetate and 3000 mL of water. A solid separated and the aqueous phase was removed. An additional 1000 mL of ethyl acetate was added and the mixture heated to 55° C. to dissolve the solids. Additional aqueous phase separated and was extracted with 500 mL of ethyl acetate. The organic phases were combined and washed with 1 liter of warm water and 500 mL of brine. Drying over magnesium sulfate and removal of the solvent gave 372 grams of a solid containing 10% ethyl acetate. Removal of the residual solvent gave a solid, melting point 169°–171° C.

EXAMPLE C-1 (Procedure C)

2-(4-chlorophenyl)-2-[(1,2,4-triazol-1-yl)methyl] butanoic Acid

To a 500 mL flask was charged 95 g (0.34 mole) of 2-(4-chlorophenyl-2-[(1,2,4-triazol-1-yl)methyl]butyramide and 95 g (0.97 mole) of 95% sulfuric add and 95 g of ice. The reaction was stirred at reflux for 55 hours, after which the reaction was cooled to 10° C. and partitioned between ethyl acetate and water. The mixture was treated with 200 g of 10% sodium hydroxide which resulted in a pH 10 aqueous phase. The organic phase was extracted with 200 g of water, then 200 g of 10% sodium hydroxide and again with 200 mL of water The aqueous phases were combined and washed with ethyl ether then acidified to pH 5 at which point a solid formed. The solid was filtered, washed with water, dried and gave 73 g (77% yield) of a white solid, melting point 182°–184° C.

EXAMPLE C-2 (Procedure C)

2-(2,4-dichlorophenyl)-2-[(1,2,4-triazol-1-yl)methyl] butanoic Acid

To a 1 liter flask was charged 170 g (0.54 mole) of 2-(2,4-dichlorophenyl-2-[(1,2,4-triazol-1-yl)methyl] butyramide and 170 g (1.73 mole) of 95% sulfuric acid and 170 g of ice. The reaction was stirred at 113° C. (reflux) for 14 days after which the reaction was cooled to 10° C. and partitioned between ethyl acetate and water. The mixture was treated with 915 mL of 14% sodium hydroxide which resulted in a pH 10 aqueous phase. The mixture was stirred for 10 minutes and the aqueous layer was removed and extracted with additional ethyl acetate. The ethyl acetate was combined, washed with water, dried and concentrated to provide a solid which was triturated with hexane; 95 g (55.8%) of starting amide was recovered.

The aqueous phase was acidified to pH 2 and 1000 mL of ethyl acetate was added and warmed to 50° C. An insoluble solid formed which was filtered, providing 28.5 g of acid. The phases were separated and the organic phase was washed with brine, dried and concentrated giving additional solid which was triturated with hexane and filtered providing 36.2 g of acid. The total product yield was 38%, melting point 206°–208° C.

EXAMPLE C-3 (Procedure C)

4-(4-chlorophenyl)-2-phenyl-2-[(1,2,4-triazol-1-yl) methyl]butanoic Acid

To a 2 liter flask was charged 220 g (0.62 mole) of 2-(4-chlorophenyl)-2-phenyl-2-[(1,2,4-triazol-1-yl)methyl] butyramide and 1000 mL (6.3 moles of 48% hydrobromic acid. The reaction was heated at 80°–85° C. for 6 days then cooled to room temperature and poured into 4 liters of ice water. The solution was extracted with 2×1000 mL of water and saturated sodium chloride solution (brine). Drying over magnesium sulfate was followed by treatment with charcoal, then filtering through Celite® and concentrating. The solid residue was slurried in ether, filtered and dried to give 139 g (63% yield), melting point 188°–190° C.

EXAMPLE 2 (Procedure D)

2-(4-chlorophenyl)-2-[(1,2,4-triazol-1-yl)methyl] hexan-1-ol

To a 3 liter flask stirring under nitrogen, fitted with a mechanical stirrer, was charged 10.2 g (0.325 mole) of lithium aluminum hydride in 400 mL of dry tetrahydrofuran. To the slurry was charged, over 45 minutes, 100 g (0.325 mole) of 2-(4-chlorophenyl)-2-[(1,2,4-triazol-1-yl)-methyl] hexanoic acid in 1600 mL of dry tetrahydrofuran. Upon addition, hydrogen gas evolved and the slurry was stirred for 2 hours. The mixture was allowed to stand overnight and was quenched by the addition of concentrated sodium sulfate solution, filtered and the solvent concentrated and again washed with water. The solvent was dried, filtered, concentrated and gave 63 g (66.3% yield) of a light yellow semisolid which solidified by trituration with ether, melting point. 113°–115° C.

EXAMPLE 77 (Procedure D)

2-(2,4-dichlorophenyl)-2-[(1,2,4-triazol-1-yl)methyl] butan-1-ol

To a 2 liter flask stirring under nitrogen, fitted with a mechanical stirrer, was charged 14.5 g (0.38 mole) of lithium aluminum hydride in 300 mL of dry tetrahydrofuran. To the slurry was charged, over 45 minutes, 60 g (0.19 mole) of 2-(2,4-dichlorophenyl)-2-[(1,2,4-triazol-1-yl)methyl] butanoic acid in 900 mL of dry tetrahydrofuran while maintaining the temperature at 10° C. The reaction was stirred for 16 hours then quenched with saturated sodium sulfate, filtered and washed with ethyl acetate. The organic phase was concentrated and gave a residue which was suspended in 500 mL ethyl acetate, washed with 500 mL water, 300 mL saturated sodium bicarbonate, and 300 mL brine. Drying and removal of the solvent gave a tacky solid which was triturated with ether and gave 15 g of solid. Trituration of the mother liquor with ether gave 2.9 g. This was repeated twice which resulted in a total of 22.1 g (38.7% yield), melting point 160°–163° C.

EXAMPLE 52 (Procedure D)

4-(4-chlorophenyl)-2-[(1,2,4-triazol-1-yl)methyl] butan-1-ol

To a 5 liter flask stirring under nitrogen, fitted with a mechanical stirrer, was charged 16 g (0.42 mole) of lithium aluminum hydride in 1000 mL of dry tetrahydrofuran. The slurry was cooled to 5° C. and 142 g (0.40 mole) of 2-(4-chlorophenyl)-2-[(1,2,4-triazol-1-yl)methyl]butanoic acid in 1500 mL of dry tetrahydrofuran was added dropwise over 4 hours maintaining the temperature at 5°–10° C. The mixture was stirred 16 hours at room temperature. The reaction was quenched at 5° C. with the addition of 500 mL of saturated sodium sulfate and the solvent removed under vacuum. The gelatinous solid was filtered with toluene which was washed with 2×1000 mL of water and 1000 mL of brine. The solvent was dried, filtered through Celite®, concentrated and gave 99 g (72.6% yield) of a viscous yellow glass which slowly crystallized, melting point 40°–45° C.

EXAMPLE 64 (Procedure E)

2-phenyl-2-[(1,2,4-triazol-1-yl)methyl]-1-hexylamine

To a 5 liter flask stirring under nitrogen, fitted with a mechanical stirrer, was charged 21 g (0.55 mole) of lithium aluminum hydride. To the lithium aluminum hydride was charged 127 g (0.50 mole) alpha-butyl-alpha-phenyl-1H-1, 2,4-triazole-1-propanenitrile in 2500 mL of dry ether over 2.5 hours. The reaction was stirred for an additional 5 hours after which GLC indicated the reaction was complete. The reaction was quenched with sodium sulfate, filtered and the organic phase separated. The aqueous phase was extracted with 1000 mL of ether. The organics were combined, washed with 3×1.5 liters of ice water, dried, filtered and concentrated without external heating and gave 88 g (69.2% yield) of a pale green oil.

EXAMPLE 76 (Procedure E)

4-(4-chlorophenyl)-2-[(1,2,4-triazol-1-yl)methyl]-1-butylamine

To a 5 liter flask stirring under nitrogen, fitted with a mechanical stirrer, was charged 18 g (0.45 mole) of lithium aluminum hydride in 1000 mL of dry tetrahydrofuran which was then cooled to 5° C. To the slurry was added 152 g (0.45 mole) of alpha-(2-(4-chlorophenyl)ethyl)-alpha-phenyl-1H-1,2,4-triazole-1-propanenitrile in 2000 mL of dry tetrahydrofuran over 3 hours. The reaction was kept at 5°–10° C. during the addition then allowed to warm to room temperature and stirred overnight. The reaction was cooled in an ice bath and quenched with the slow addition of sodium sulfate. The solvent was removed and the residue was extracted with ethyl acetate and washed with 1000 mL water and 1000 mL brine. After drying, and removal of the solvent, 137 g (89.5% yield) of a very viscous oil resulted.

EXAMPLE 11 (Procedure F)

2-(4-chlorophenyl)-2-[(1,2,4-triazol-1-yl)methyl] hexyl acrylate

To a 100 mL flask stirring under nitrogen was charged 2.88 g (0.0098 mole) of 2-(4-chlorophenyl)-2-[(1,2,4-triazol-1-yl)methyl]hexan-1-ol in 25 mL of tetrahydrofuran. To the mixture was added 2.5 mL of pyridine followed by 1.0 g (0.011 mole) of acryloyl chloride after which a precipitate formed. The reaction was monitored by GLC and was 60% complete after 1 hour. An additional 1.0 g of acryloyl chloride was added followed by 20 mL of dimethylformamide. The reaction was stirred at 60° C. until the precipitate dissolved and was then stirred overnight at room temperature. The reaction was quenched with 20 mL water and extracted with 10 mL ethyl acetate, washed with 2×10 mL water and 2×20 mL saturated sodium bicarbonate. The solvent was dried and concentrated; the residue was chromatographed on 50 g of silica gel. The product was eluted with a 1 to 1 mixture of hexane and ethyl acetate and gave 1.72 g (50.4% yield) of an oil.

EXAMPLE 29 (Procedure F)

2-(4-chlorophenyl)-2-[(1,2,4-triazol-1-yl)methyl] hexyl 4-chlorophenylurethane

To a 100 mL flask was charged 3.0 g of 2-(4-chlorophenyl)-2-[(1,2,4-triazol-1-yl)methyl]hexan-1-ol (0.010 mole, 1.0eq.) in 60 mL of chloroform followed by 0.5 g of triethylamine. The mixture was stirred at room temperature for 15 minutes after which 1.5 g of p-chlorophenylisocyanate (0.010 mole, 1.0eq.) was added dropwise. The reaction was stirred at reflux for 24 hours then quenched with water and methylene chloride. The solvent was concentrated and gave 5.0 g of crude product. The product was chromatographed (4 to 1 mixture of ethyl acetate and hexane) and gave 3.0 g (66% yield) of a light yellow glassy solid, melting point 70°–75° C.

EXAMPLE 66 (Procedure H)

N-{2-phenyl-2-[(1,2,4-triazol-1 -yl)methyl] hexyl}acetamide

To a 100 mL flask stirring under nitrogen was charged 2.58 g (0.010 mole) of 2-phenyl-2-[(1,2,4-triazol-1-yl) methyl]-1-hexylamine and 15 mL of acetic anhydride. To the mixture was added 1.5 mL of pyridine and the reaction was stirred at room temperature for 3 hours. After GLC indicated the reaction was complete, it was quenched with 20 mL of water and 100 mL of ether after the acetic anhydride and pyridine were removed under vacuum. The residue was dissolved in ether and washed with 2×50 mL water and 2×50 mL of saturated sodium bicarbonate. The organic phase was dried, concentrated and gave 2.68 g (89.3% yield) of a solid, melting point 112°–115° C.

EXAMPLE 21 (Procedure I)

1-[2-(4-chlorophenyl)-2-(methoxymethyl)hexyl]-1,2, 4-triazole

To a 100 mL 3 neck flask stirring under nitrogen was charged 0.40 g (0.010 mole) of 60% sodium hydride, prewashed with hexanes, in 30 mL of dimethylformamide. The slurry was cooled to 10° C. and 2.12 g (0.00723 mole) of 2-(4-chlorophenyl)-2-[(1,2,4-triazol-1-yl)methyl]hexan-1-ol in 15 mL of dimethylformamide was added over 15 minutes. The reaction was warmed to room temperature and 1.17 g (0.00812 mole) of methyl iodide was added directly and the reaction was stirred overnight at room temperature. The reaction was quenched with 10 mL water and 100 mL ether. The organic phase was washed with 2×25 mL water, dried, concentrated and gave 1.53 g (69% yield) of product as an oil.

EXAMPLE 62 (Procedure I)

1-[4-(4-chlorophenyl)-2-phenyl-2-(propargyloxymethyl)butyl]-1,2,4-triazole

To a 250 mL 3 neck flask stirring under nitrogen was charged 1.1 g (0.022 mole) of 60% sodium hydride, prewashed with hexanes, in 40 mL of dimethylformamide. The slurry was stirred at room temperature and 5.12 g (0.015 mole) of 4-(4-chlorophenyl)-2-phenyl-[(1,2,4-triazol-1-yl) methyl]butan-1-ol in 30 mL of dimethylformamide was added over 5 minutes. The slurry was stirred for 45 minutes after which 2.45 g (0.0165 mole) of propargyl bromide was added. After 4 hours GLC indicated the starting alcohol was consumed; the reaction was quenched with 20 mL water and 75 mL ether. The organic phase was separated, washed with 2×50 mL water, decolorized with charcoal, filtered through Celite®, concentrated, and gave 4.19 g (70.7% yield) of product as an oil.

EXAMPLE 39 (Procedure I)

2-[2-(4-chlorophenyl)-2-[(1,2,7-triazol-1-yl)methyl] hexyloxy]pyrimidine

To a flask was charged 0.15 g (0.0034 mole) of 60% sodium hydride, washed with 2×30 mL hexane, in 20 mL of tetrahydrofuran. While stirring at room temperature, 10 g (0.0034 mole) of 2-(4-chlorophenyl)-2-[(1,2,4-triazol-1-yl) methyl]hexan-1-ol was added. The slurry was stirred at room temperature and 0.39 g of 2-chloropyrimidine (0.0034 mole) was added. The reaction was stirred overnight after which TLC using ethyl acetate indicated the reaction was complete. The product was isolated from ether after quenching and washing with water. After drying and removal of the solvent, 1.30 g (100% yield) of an oil resulted.

EXAMPLE 9 (Procedure G)

2-(4-chlorophenyl)-2-[(1,2,4-triazol-1-yl)methyl] hexylmethanesulfonate

To a 200 mL 3 neck flask stirring under nitrogen was charged 8.76 g (0.030 mole)2-(4-chlorophenyl)-2-[(1,2,4-triazol-1-yl)methyl]- hexan-1-ol in 40 mL of methylene chloride. The solution was cooled to 10° C. and 6.3 mL (0.045 mole) of triethylamine was added followed by 2.5 mL (0.033 mole) of methanesulfonyl chloride. After 1 hour an additional 3.1 mL of triethylamine and 1.75 mL of methanesulfonyl chloride were added. After 6 hours the reaction was 70% complete and was quenched with 15 mL water and extracted with 150 mL of methylene chloride. After washing with 2×50 mL water and 50 mL of 10% hydrochloric acid, the organic please was dried and concentrated. The product was chromatographed on 100 g of silica gel and eluted with a 1 to 1 mixture of ether and ethyl acetate and gave 6.5 g (57.2% yield) of product as a thick oil.

Table 1 lists certain compounds of the invention, along with their melting points. For those compounds for which melting points were not obtainable, elemental analyses are given in Table 2 or, alternatively, NMR shifts in Table 3.

It will be obvious to one or ordinary skill in this art that the compounds of Table 1 and other compounds of the invention may be prepared by substituting appropriate starting materials in the reactions illustrated in Scheme 1.

TABLE 1

$$\underset{Z}{\overset{T\text{—}}{\underset{|}{C_6H_4}}}\text{—}\underset{|}{\overset{CH_2-W}{C}}\text{—}CH_2\text{—}N(\text{triazole})$$

| Ex. No. | Method | T | Z | W | Melting Point (°C.) |
|---|---|---|---|---|---|
| 1 | D | H | n-C$_4$H$_9$ | OH | 84–85 |
| 2 | D | 4Cl | n-C$_4$H$_9$ | OH | 113–115 |
| 3 | D | 2OH | n-C$_4$H$_9$ | OH | 62–65 |
| 4 | F | H | n-C$_4$H$_9$ | Cl | OIL |
| 5 | F | H | n-C$_4$H$_9$ | OCOCH$_3$ | OIL |
| 6 | G | H | n-C$_4$H$_9$ | OSO$_2$CH$_3$ | OIL |
| 7 | F | 2OCOCH$_3$ | n-C$_4$H$_9$ | OCOCH$_3$ | OIL |
| 8 | F | 4Cl | n-C$_4$H$_9$ | OCOCH$_3$ | OIL |
| 9 | G | 4Cl | n-C$_4$H$_9$ | OSO$_2$CH$_3$ | OIL |
| 10 | F | H | n-C$_4$H$_9$ | OCOCH=CH$_2$ | OIL |
| 11 | F | 4Cl | n-C$_4$H$_9$ | OCOCH=CH$_2$ | OIL |
| 12 | I | H | n-C$_4$H$_9$ | OSi(CH$_3$)$_2$(t-C$_4$H$_9$) | OIL |
| 13 | I | 4Cl | n-C$_4$H$_9$ | OSi(CH$_3$)$_2$(t-C$_4$H$_9$) | OIL |
| 14 | F | H | n-C$_4$H$_9$ | OCOCH$_2$Cl | 79–80 |
| 15 | F | 4Cl | n-C$_4$H$_9$ | OCOCH$_2$Cl | 93–94 |
| 16 | F | H | n-C$_4$H$_9$ | OCOC(CH$_3$)$_3$ | OIL |
| 17 | F | 4Cl | n-C$_4$H$_9$ | OCOC$_6$H$_5$ | OIL |
| 18 | F | 4Cl | n-C$_4$H$_9$ | OCOC$_6$H$_3$(2,4Cl) | 85–87 |
| 19 | F | 4Cl | n-C$_4$H$_9$ | OCOC$_6$H$_3$(3,5Cl) | 129–130 |
| 20 | F | 4Cl | n-C$_4$H$_9$ | OCOCH$_2$C$_6$H$_5$ | OIL |
| 21 | I | 4Cl | n-C$_4$H$_9$ | OCH$_3$ | OIL |
| 22 | I | 4Cl | n-C$_4$H$_9$ | OCH$_2$C$_6$H$_3$(2,4Cl) | OIL |
| 23 | I | 4Cl | n-C$_4$H$_9$ | OCH$_2$CH=CH$_2$ | OIL |
| 24 | I | 4Cl | n-C$_4$H$_9$ | OCH$_2$OCOC(CH$_3$)$_3$ | OIL |
| 25 | I | 4Cl | n-C$_4$H$_9$ | OCH$_2$C≡CH | OIL |
| 26 | I | H | n-C$_4$H$_9$ | OCH$_2$(2PYRIDYL) | OIL |
| 27 | I | H | n-C$_4$H$_9$ | OCH$_2$(4PYRIDYL) | OIL |
| 28 | I | 4Cl | n-C$_4$H$_9$ | OCH$_2$CH$_2$OC$_2$H$_5$ | OIL |
| 29 | F | 4Cl | n-C$_4$H$_9$ | OCONHC$_6$H$_4$(4Cl) | 70–75 |
| 30 | F | 4Cl | n-C$_4$H$_9$ | OCO-c-C$_3$—H$_5$ | OIL |
| 31 | I | 4Cl | n-C$_4$H$_9$ | OCH$_2$CH$_3$ | OIL |
| 32 | F | 4Cl | n-C$_4$H$_9$ | OCOCH$_2$OC$_6$H$_4$(4Cl) | OIL |
| 33 | F | 4Cl | n-C$_4$H$_9$ | OCOCH$_2$C$_6$H$_4$(4Cl) | OIL |
| 34 | F | 4Cl | n-C$_4$H$_9$ | OCO(2-FURYL) | OIL |
| 35 | F | 4Cl | n-C$_4$H$_9$ | OCOCCl$_3$ | OIL |
| 36 | F | 4Cl | n-C$_4$H$_9$ | OCH$_2$(3PYRIDYL) | OIL |
| 37 | F | 4Cl | n-C$_4$H$_9$ | OCOCH=CHC$_6$H$_5$ | OIL |
| 38 | F | 4Cl | n-C$_4$H$_9$ | OCOC$_6$H$_4$(4OCH$_3$) | OIL |
| 39 | I | 4Cl | n-C$_4$H$_9$ | O(2PYRIMIDINYL) | OIL |
| 40 | I | 4Cl | n-C$_4$H$_9$ | O(2PYRIDYL) | OIL |
| 41 | I | 4Cl | n-C$_4$H$_9$ | OCH$_2$(1H-1,2,4-triazolyl) | OIL |
| 42 | I | 4Cl | n-C$_4$H$_9$ | O(PYRAZINYL) | OIL |
| 43 | F | 4Cl | n-C$_4$H$_9$ | OCOCH$_2$C$_6$H$_4$(4F) | OIL |
| 44 | F | 4Cl | n-C$_4$H$_9$ | OCOCH$_2$C$_6$H$_4$(4CF$_3$) | OIL |
| 45 | F | 4Cl | n-C$_4$H$_9$ | OCOCH$_2$C$_6$H$_3$(2,4Cl) | OIL |
| 46 | F | 4Cl | n-C$_4$H$_9$ | OCOCH$_2$C$_6$H$_4$(4Br) | OIL |
| 47 | F | 4Cl | n-C$_4$H$_9$ | OCOCF$_3$ | GLASS |
| 48 | F | 4Cl | n-C$_4$H$_9$ | OPO(OEt)$_2$ | OIL |
| 49 | F | 4Cl | n-C$_4$H$_9$ | OPO(OC$_2$H$_5$)$_2$ | OIL |
| 50 | F | 4Cl | n-C$_4$H$_9$ | OCOCH$_2$(2-THIENYL) | OIL |
| 51 | F | 4Cl | n-C$_4$H$_9$ | OCOCF$_2$CF$_2$CF$_3$ | OIL |
| 52 | D | H | CH$_2$CH$_2$C$_6$H$_4$(4Cl) | OH | 40–45 |
| 53 | F | H | CH$_2$CH$_2$C$_6$H$_4$(4Cl) | OCOCH$_2$C$_6$H$_5$ | OIL |
| 54 | F | H | CH$_2$CH$_2$C$_6$H$_4$(4Cl) | OCOCH$_3$ | OIL |
| 55 | F | H | CH$_2$CH$_2$C$_6$H$_4$(4Cl) | OCO(2-FURYL) | OIL |
| 56 | I | H | CH$_2$CH$_2$C$_6$H$_4$(4Cl) | OCH$_3$ | OIL |
| 57 | F | H | CH$_2$CH$_2$C$_6$H$_4$(4Cl) | OCOC$_6$H$_5$ | OIL |
| 58 | I | H | CH$_2$CH$_2$C$_6$H$_4$(4Cl) | OCH$_2$CH=CH$_2$ | OIL |
| 59 | I | 2,4Cl | n-C$_4$H$_9$ | OCH$_2$CH$_2$OC$_2$H$_5$ | OIL |
| 60 | I | 2,4Cl | n-C$_4$H$_9$ | O(i-C$_3$H$_7$) | RESIN |
| 61 | D | 2,4Cl | n-C$_4$H$_9$ | OH | 220–221 |
| 62 | I | H | CH$_2$CH$_2$C$_6$H$_4$(4Cl) | OCH$_2$C≡CH | OIL |
| 63 | D | 4Cl | C$_2$H$_5$ | OH | 125–126 |
| 64 | E | H | n-C$_4$H$_9$ | NH$_2$ | OIL |
| 65 | E | 4Cl | n-C$_4$H$_9$ | NH$_2$ | OIL |
| 66 | H | H | n-C$_4$H$_9$ | NHCOCH$_3$ | 112–115 |
| 67 | H | 4Cl | n-C$_4$H$_9$ | NHCOCH$_3$ | GLASS |
| 68 | H | 4Cl | n-C$_4$H$_9$ | NHCOCH$_2$C$_6$H$_5$ | GLASS |

TABLE 1-continued

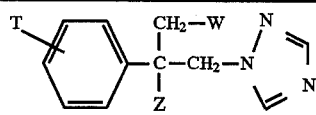

| Ex. No. | Method | T | Z | W | Melting Point (°C.) |
|---|---|---|---|---|---|
| 69 | H | 4Cl | n-$C_4H_9$ | NHCO$C_6H_5$ | GLASS |
| 70 | H | 4Cl | n-$C_4H_9$ | NHCO(2-FURYL) | GLASS |
| 71 | H | 4Cl | n-$C_4H_9$ | NHCO-c-$C_3H_5$ | OIL |
| 72 | H | 4Cl | n-$C_4H_9$ | NHCOCH$_2$Cl | OIL |
| 73 | H | 4Cl | n-$C_4H_9$ | NHCOCCl$_3$ | OIL |
| 74 | H | 4Cl | n-$C_4H_9$ | NHCOCH=CH$_2$ | OIL |
| 75 | E | 4Cl | n-$C_4H_9$ | NH$_2$ | OIL |
| 76 | E | H | CH$_2$CH$_2$C$_6$H$_4$(4Cl) | NH$_2$ | OIL |
| 77 | D | 2,4Cl | $C_2H_5$ | OH | 160–163 |
| 78 | E | 2,4Cl | $C_2H_5$ | NH$_2$ | OIL |

TABLE 2

Elemental Analyses for
Carbon, Hydrogen, Nitrogen, Oxygen, Chlorine and Others

| Ex. No. | Analysis | Carbon | Hydrogen | Nitrogen | Oxygen | Chlorine |
|---|---|---|---|---|---|---|
| 4 | Calculated | 64.83 | 7.26 | 15.13 | | |
| | Found | 69.27 | 7.37 | 15.93 | | |
| 5 | Calculated | 67.73 | 7.70 | 13.95 | 10.62 | |
| | Found | 67.31 | 7.38 | 13.95 | 11.56 | |
| 6 | Calculated | 56.93 | 6.87 | 12.45 | 14.23 | |
| | Found | 55.63 | 7.37 | 11.76 | 13.43 | |
| 7 | Calculated | 63.47 | 7.01 | 11.69 | 17.81 | |
| | Found | 63.03 | 7.32 | 12.09 | 17.55 | |
| 8 | Calculated | 60.59 | 6.89 | 12.48 | 9.51 | 10.53 |
| | Found | 61.27 | 6.73 | 12.26 | 9.43 | 10.42 |
| 10 | Calculated | 68.96 | 7.40 | 13.42 | 11.56 | |
| | Found | 67.42 | 7.64 | 13.65 | 10.22 | |
| 11 | Calculated | 62.13 | 6.38 | 12.09 | 9.20 | 10.20 |
| | Found | 61.61 | 6.50 | 12.01 | 9.30 | 10.11 |
| 12 | Calculated | 67.44 | 9.45 | 11.25 | 4.28 | |
| | Found | 67.10 | 7.87 | 12.40 | 10.96 | |
| 13 | Calculated | 61.79 | 8.40 | 10.30 | 3.92 | 8.69 |
| | Found | 62.24 | 8.22 | 10.74 | 0.76 | 8.70 |
| 17 | Calculated | 66.38 | 6.08 | 10.57 | 8.05 | 8.97 |
| | Found | 66.64 | 6.05 | 8.44 | 11.20 | 7.66 |
| 21 | Calculated | 62.41 | 7.29 | 13.66 | 5.70 | 11.52 |
| | Found | 62.68 | 7.25 | 13.14 | 5.69 | 11.58 |
| 22 | Calculated | 64.74 | 7.25 | 12.50 | 4.80 | 10.68 |
| | Found | 64.69 | 7.25 | 11.83 | 5.43 | 10.47 |
| 23 | Calculated | 58.33 | 5.35 | 9.28 | 3.53 | 23.50 |
| | Found | 57.09 | 5.23 | 8.33 | 4.27 | 25.08 |
| 24 | Calculated | 61.80 | 7.42 | 10.30 | 11.77 | 8.70 |
| | Found | 61.38 | 7.38 | 10.22 | 11.75 | 9.02 |
| 25 | Calculated | 65.12 | 6.69 | 12.67 | 4.82 | 10.70 |
| | Found | 64.31 | 6.74 | 12.16 | 5.92 | 10.63 |
| 26 | Calculated | 71.95 | 7.48 | 15.99 | | |
| | Found | 69.98 | 7.32 | 16.22 | | |
| 27 | Calculated | 71.95 | 7.48 | 15.99 | | |
| | Found | 68.37 | 7.31 | 15.37 | | |
| 28 | Calculated | 62.86 | 6.95 | 11.58 | 8.82 | 9.77 |
| | Found | 61.89 | 7.31 | 11.12 | 10.10 | 9.72 |
| 30 | Calculated | 63.04 | 6.69 | 11.62 | 8.85 | 9.80 |
| | Found | 62.06 | 6.74 | 11.52 | 9.97 | 9.81 |
| 32 | Calculated | 58.65 | 5.60 | 9.33 | 10.66 | 15.75 |
| | Found | 58.64 | 5.51 | 8.77 | 10.94 | 15.96 |
| 33 | Calculated | 61.86 | 5.65 | 9.42 | 7.17 | 15.89 |
| | Found | 61.35 | 5.60 | 9.07 | 7.91 | 15.88 |
| 34 | Calculated | 60.69 | 5.90 | 11.18 | 12.77 | 9.44 |
| | Found | 61.35 | 5.76 | 10.87 | 12.84 | 9.22 |
| 35 | Calculated | 46.47 | 4.36 | 9.53 | 7.18 | 32.30 |
| | Found | 46.44 | 4.42 | 9.17 | 7.87 | 32.04 |
| 36 | Calculated | 65.51 | 6.55 | 14.56 | 4.16 | 9.22 |
| | Found | 64.95 | 6.55 | 14.31 | 5.04 | 9.23 |
| 37 | Calculated | 67.98 | 6.19 | 9.92 | 7.55 | 8.37 |
| | Found | 68.02 | 6.31 | 9.36 | 8.76 | 7.75 |
| 38 | Calculated | 64.53 | 6.13 | 9.83 | 11.22 | 8.29 |
| | Found | 63.87 | 6.12 | 9.20 | 13.27 | 7.70 |
| 43 | Calculated | 64.23 | 5.87 | 9.78 | 7.45 | 8.25 |
| | Found | 64.02 | 5.75 | 9.52 | 8.44 | 7.94 |
| 44 | Calculated | 60.64 | 5.25 | 8.76 | 6.67 | 7.39 |
| | Found | 59.91 | 5.21 | 8.44 | 7.54 | 7.09 |
| 45 | Calculated | 57.43 | 5.03 | 8.74 | 6.66 | 22.13 |
| | Found | 57.35 | 4.98 | 7.91 | 7.97 | 21.45 |
| 46 | Calculated | 56.26 | 5.14 | 8.57 | 6.52 | 7.22 |
| | Found | 56.46 | 5.26 | 8.19 | 7.58 | 6.28 |
| 47 | Calculated | 52.15 | 4.91 | 10.79 | 8.21 | 9.09 |
| | Found | 52.15 | 5.39 | 10.86 | 8.32 | 9.49 |
| 48 | Calculated | 53.06 | 6.80 | 9.78 | 14.89 | 8.25 |
| | Found | 54.22 | 6.84 | 10.64 | 12.30 | 9.06 |
| 49 | Calculated | 59.45 | 5.49 | 10.41 | 7.93 | 8.78 |
| | Found | 58.35 | 5.58 | 8.79 | 10.98 | 7.22 |
| 50 | Calculated | 60.32 | 5.79 | 10.06 | 7.66 | 8.49 |
| | Found | 60.33 | 5.77 | 9.59 | 9.30 | 7.48 |
| 51 | Calculated | 46.56 | 3.92 | 8.58 | 6.54 | |
| | Found | 46.89 | 4.07 | 8.97 | 7.24 | |
| 53 | Calculated | 70.48 | 5.70 | 9.14 | 6.96 | 7.71 |
| | Found | 70.09 | 5.91 | 9.19 | 7.60 | 7.47 |
| 54 | Calculated | 65.68 | 5.78 | 10.95 | 8.34 | 9.24 |
| | Found | 65.56 | 6.13 | 10.41 | 7.03 | 8.83 |
| 55 | Calculated | 66.11 | 5.09 | 9.64 | 11.01 | 8.13 |
| | Found | 64.82 | 5.17 | 8.59 | 14.57 | 6.73 |
| 56 | Calculated | 67.48 | 6.23 | 11.81 | 4.49 | 9.97 |
| | Found | 66.44 | 6.51 | 11.79 | 5.67 | 9.82 |
| 57 | Calculated | 69.85 | 5.64 | 9.41 | 7.16 | 7.94 |
| | Found | 70.15 | 5.74 | 9.23 | 8.80 | 5.90 |
| 58 | Calculated | 69.35 | 6.09 | 11.04 | 4.20 | 9.31 |
| | Found | 68.49 | 6.37 | 10.74 | 5.04 | 9.22 |
| 62 | Calculated | 69.53 | 5.84 | 11.06 | 4.21 | 9.34 |
| | Found | 69.76 | 6.02 | 10.59 | 5.22 | 8.94 |
| 64 | Calculated | 69.71 | 8.59 | 21.69 | | |
| | Found | 68.76 | 8.86 | 20.54 | | |
| 65 | Calculated | 61.51 | 7.23 | 19.14 | | 12.11 |
| | Found | 62.59 | 7.48 | 17.43 | | 12.03 |
| 67 | Calculated | 60.96 | 6.92 | 16.34 | 4.79 | 10.59 |
| | Found | 61.59 | 6.91 | 15.39 | 5.51 | 10.27 |
| 68 | Calculated | 67.20 | 6.62 | 13.64 | 3.89 | 8.63 |
| | Found | 67.13 | 6.61 | 12.97 | 4.93 | 8.61 |
| 69 | Calculated | 66.55 | 6.35 | 14.72 | 4.63 | 8.94 |
| | Found | 66.27 | 6.25 | 13.36 | 5.34 | 8.60 |
| 70 | Calculated | 62.07 | 5.99 | 14.49 | 8.28 | 9.17 |
| | Found | 62.08 | 6.29 | 13.42 | 8.85 | 8.67 |
| 71 | Calculated | 63.21 | 6.99 | 15.53 | 4.44 | 9.83 |

TABLE 2-continued

Elemental Analyses for
Carbon, Hydrogen, Nitrogen, Oxygen, Chlorine and Others

|    |            | C     | H     | N     | O    | Cl/Other |
|----|------------|-------|-------|-------|------|----------|
|    | Found      | 6.02  | 7.06  | 14.61 | 6.27 | 9.14     |
| 72 | Calculated | 55.27 | 6.01  | 15.18 | 4.34 |          |
|    | Found      | 53.30 | 6.55  | 13.35 | 9.99 |          |
| 73 | Calculated | 46.58 | 4.60  | 12.19 | 3.65 | 32.37    |
|    | Found      | 47.35 | 4.72  | 12.15 | 4.77 | 31.00    |
| 74 | Calculated | 62.31 | 6.64  | 16.16 | 4.61 | 10.22    |
|    | Found      | 61.76 | 6.93  | 14.92 | 6.35 | 9.89     |
| 75 | Calculated | 55.03 | 17.12 |       |      | 21.67    |
|    | Found      | 55.10 | 5.88  | 14.40 |      | 20.87    |
| 76 | Calculated | 66.93 | 6.21  | 16.44 |      | 10.40    |
|    | Found      | 67.78 | 6.24  | 14.22 |      | 10.18    |
| 78 | Calculated | 52.16 | 5.39  | 18.73 |      | 23.71    |
|    | Found      | 53.93 | 5.49  | 15.06 |      | 23.95    |

| Ex. No. | Analysis   | Silicon | Fluorine | Bromine | Sulfur | Phosphorous |
|---------|------------|---------|----------|---------|--------|-------------|
| 12      | Calculated | 7.51    |          |         |        |             |
|         | Found      | 7.02    |          |         |        |             |
| 13      | Calculated | 6.88    |          |         |        |             |
|         | Found      | 5.68    |          |         |        |             |
| 43      | Calculated |         | 4.42     |         |        |             |
|         | Found      |         | 4.45     |         |        |             |
| 44      | Calculated |         | 11.88    |         |        |             |
|         | Found      |         | 12.28    |         |        |             |
| 46      | Calculated |         |          | 16.29   |        |             |
|         | Found      |         |          | 16.23   |        |             |
| 48      | Calculated |         |          |         |        | 7.21        |
|         | Found      |         |          |         |        | 5.34        |
| 49      | Calculated |         |          |         | 7.94   |             |
|         | Found      |         |          |         | 9.92   |             |
| 50      | Calculated |         |          |         | 76.8   |             |
|         | Found      |         |          |         | 8.16   |             |
| 51      | Calculated |         | 27.16    |         |        |             |
|         | Found      |         | 25.36    |         |        |             |

TABLE 3 - NMR shifts for Compounds of the Invention

EX.No. 9 NMR:60 MHz (CDCl$_3$) 1.0–2.0(m,9H), 3.3(s, 3H), 4.4–4.8(ABq,4H), 7.0–7.6(ABq,4H), 7.8(s,1H), and 8.0(s, 1H).

EX.No. 16 NMR:90 MHz (CDCl$_3$) 0.9–1.9(m,9H), 1.2(br s,9H), 4.2–4.6(ABq,2H), 4.5(br s,2H),7.1–7.5(m,6H), and 7.9(s, 1H).

EX.No. 20 NMR:90 MHz (CDCl3) 0.8–1.8(m,9H), 3.7 (s,2H), 4.0–4.5(m,4H), 7.9–8.4(m,10H), and 7.9(s,1H).

EX.No. 31 NMR:90 MHz (CDCl$_3$) 0.8–1.8(m,12H), 3.3–3.8(m,4H), 4.5(br s,2H), 7.0–7.3(ABq,2H), 7.8(s, 1H), and 7.9(s, 1H).

EX.No. 39 NMR:90 MHz (CDCl$_3$) 0.8–2.0(m,9H), 4.2–4.8(ABq,2H), 4.6(s,2H), 6.9–7.0(t, 1H), 7.2–7.4(ABq, 4H), 7.8(s,1H), 7.9(s,1H), 8.5(s, 1H), and 8.6(s,1H).

EX.No. 40 NMR:90 MHz (CDCl$_3$) 0.8–2.0(m,9H), 4.2–4.8(ABq, 2H), 4.8(s,2H), 6.9–7.0(t,1H), 7.4(s,1H), 7.6 (m,1H), 7.7(s,1H) 7.8(s, 1H), and 8.0–8.2(m,1H).

EX.No. 41 NMR:90 MHz (CDCl$_3$) 0.8–2.0(m,9H), 3.6–4.0(ABq,2H), 4.2–4.6(ABq,2H), 5.6(s,2H), 6.8–7.4 (ABq,4H), 7.4(s,1H), 7.8(s,1H), 8.0(s, 1H), and 8.3(s,1H).

EX.No. 42 NMR:90 MHz (CDCl$_3$) 0.8–2.0(m,9H), 4.4–4.8(ABq,2H), 4.6(s,2H), 7.0–7.4(ABq,2H),7.6(s,1H), 7.8(s,1H), 8.0–8.2(m,2.H), and 8.4(s, 1H).

EX.No. 59 NMR:60 MHz (CDCl$_3$) 1.0–1.3(t,3H), 1.0–2.2 (m,9H), 3.3–3.8(two overlapping ABq,4H), 4.3–4.5(m,2H), 4.9–5.0(ABq,2H),6.9–7.5(m,3H), 7.3(s,1H), and 7.8(s, 1H).

EX.No. 60 NMR:60 MHz (CDCl$_3$)0.8–2.2(m,9H), 1.2(s, 3H), 1.3(s,3H),4.7–5.2(ABq,2H), 5.1–5.3(t, 1H), 6.8–7.2(d, 1H), 7.2–7.4(dd,1H), 7.6(d, 1H), 7.4(o, 1H), and 8.0(s,1H).

EX.No. 61 NMR:60 MHz (CDCl$_3$) 0.9–2.0 (m, 9H), 2.0–2.2 (br 5, 2H), 5.0–5.2 (br 5, 2H), 7.1–7.5 (m, 2H), 7.9–8.0 (m, 2H).

The 1,2,4-triazoles, and the enantiomorphs, acid addition salts and metal salt complexes thereof are useful as agricultural fungicides and, as such, can be applied to various loci such as the seed, the soil or the foliage. When used as herbicides, the compounds may be applied either to the plant itself or to the locus where control of undesired vegetation is needed. For such purposes these compounds can be used in the technical or pure form as prepared, as solutions or as formulations. The compounds are usually taken up in a carrier or are formulated so as to render them suitable for subsequent dissemination. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of a 1,2,4-triazole, 45 parts of a synthetic precipitated hydrated silicon dioxide, such as that sold under the trademark Hi—SilR, and 5 parts of sodium lignosulfonate. In another preparation a kaolin type (Barden) clay is used in place of the Hi—Sil in the above wettable powder, and in another such preparation 25% of the Hi—Sil is replaced with a synthetic sodium silicoaluminate sold under the trademark Zeolex®7.

Dusts are prepared by mixing the 1,2,4- triazoles, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The 1,2,4-triazoles, and the enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.05 pound to about 50 pounds per acre of the active ingredient.

As a seed protectant, the amount of toxicant coated on the seed is usually at a dosage rate of from about 0.05 to about 20, preferably from about 0.05 to about 4, and more preferably from about 0.1 to about 1 ounce per hundred pounds of seed. As a soil fungicide the chemical can be incorporated in the soil or applied to the surface usually at a rate of from about 0.02 to about 20, preferably from about 0.05 to about 10, and more preferably from about 0.1 to about 5 pounds per acre. As a foliar fungicide, the toxicant is usually applied to growing plants at a rate of from about 0.01 to about 10, preferably from about 0.02 to 5, and more preferably from about 0.25 to about 1 pound per acre. pounds per acre.

Fungicides which can be combined with the compounds of this invention include:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-di chlorophenyl)-5-methyl-5-(methoxymethyl)-1,3-oxazolidi-2,4-odione, 3-(3,5-dichlorophenyl)-1-isopropylcarbamoylhydantoin, 2-cyano-[N-(ethylaminocarbonyl)-2-methoximin-] acetamide, fenpropimorph, fenpropidine, 2,6-dimethyl-N-tridecylmorpholine, dodemorph, and triforine;

(d) miscellaneous halogenated fungicities such as: chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) miscellaneous fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate sulfonate, methyl isothiocyanate, 1-thiocyano-2,4-dinitrobenzene, 1-phenylthiosemicarbazide, nickel-containing compounds, calciumcyanamide, lime sulfur, thiophanate-methyl, flutolanil, edinophos, isoprothiolane, propenazole, and tricyclazole.

The 1,2,4-triazoles, and the enantiomorphs, acid addition salts and metal salt complexes thereof can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

Numerous compounds of this invention were tested for fungicidal activity in vivo against wheat powdery mildew (WPM), wheat stem rust (WSR), rice blast (RB), rice sheath blight (RSB), and wheat leaf rust (WLR). In tests on cereals (except rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone and methanol, sprayed onto the plants, allowed to dry (four to six hours) and then the plants were inoculated with the fungus. Each test utilized control plants which were sprayed with the water, acetone and methanol mixture and inoculated with the fungus. The remainder of the technique of each of the tests is given below and the results are reported in Table 4 as percent disease control (percentages of plants treated with the compounds of the present invention lacking disease signs or symptoms compared to the untreated control plants).

Wheat Powdery Mildew (WPM)

*Erysiphe graminis* (f. sp. tritici) was cultured on wheat seedlings in a controlled temperature room at 65° to 70° F. Mildew spores were shaken from the culture plants onto wheat seedlings which had been previously sprayed with the fungicide compound. The inoculated seedlings were kept in a controlled temperature room at 65° to 75° F. and subirrigated. The percent disease control was rated 8 to 10 days after the inoculation.

Wheat Stem Rust (W.S.R.)

*Puccinia graminis* (f. sp. tritici Race 15B-2) was cultured on Wanzer wheat seedlings for a period of 14 days in a greenhouse. A water suspension of the spores from infested plants was obtained and the spore concentration was adjusted to about 2×105 spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° to 85° F.) for about 24 hours, then placed in a greenhouse environment (70° to 75° F.). Seven to eight days after inoculation, the percent disease control was determined.

Rice Sheath Blight (RSB)

*Pellicularia filamentosa* f. sp. sasiki was cultured on an autoclaved mixture of crushed rice seeds and potato dextrose broth (100 gms of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for five days in a humidity cabinet (85° to 90° F.). Percent disease controls were determined immediately after removing the seedlings from the cabinet.

Wheat Leaf Rust (WLR)

*Puccinia recondita* (f. sp. tritici Races PKB and PLD) was cultured on 7 day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for 2 minutes at 40° F. before use. A spore suspension is prepared from dry uredia by adding 20mg (9.5 million spores) per mL of Soltrol oil. The suspension is dispensed into gelatin capsules (0.7 mL capacity) which attach to the oil atomizers. One capsule is used per flat of twenty of the 2 inch square pots of 7 day old Fielder wheat. After waiting for at least 15 minutes for the oil to evaporate from the wheat leaves, the plants are placed in a dark mist chamber (18°–20° C. and 100% relative humidity) for 24 hours. The plants are then put in the greenhouse for the latent period and scored after 10 days for disease levels. For protective and curative tests, the plants are inoculated one day or two days, respectively, before spraying the plants with the fungicide compounds.

TABLE 4

Fungicidal Efficacy of Compounds of the Invention.

| Ex. No. | Rate[1] | RB[2] | RSB[3] | WLR[4] | WPM[5] | WSR[6] |
|---|---|---|---|---|---|---|
| 1 | b | —[7] | — | — | — | — |
| 2 | c | 0 | 20 | — | 100 | 100 |
| 3 | c | 0 | 35 | — | 100 | 99 |
| 4 | c | 93 | 0 | — | 94 | 99 |
| 5 | c | 100 | 0 | — | 100 | 35 |
| 6 | c | 100 | 45 | — | 45 | 90 |
| 7 | c | 0 | 45 | — | 97 | 90 |
| 8 | c | 0 | 50 | — | 100 | 100 |
| 9 | c | 85 | 0 | — | 85 | 100 |
| 10 | c | 0 | 0 | — | 50 | 90 |
| 11 | c | 20 | 0 | — | 100 | 100 |
| 12 | c | 0 | 0 | — | 90 | 60 |
| 13 | c | 0 | 0 | — | 100 | 95 |
| 14 | c | 90 | 0 | — | 100 | 75 |
| 15 | c | 80 | 50 | — | 95 | 95 |
| 16 | c | 95 | 0 | — | 75 | 80 |
| 17 | c | 85 | 0 | — | 100 | 100 |
| 18 | c | 90 | 0 | — | 90 | 0 |
| 19 | c | 100 | — | — | 90 | 0 |
| 20 | c | 100 | 0 | — | 100 | 85 |
| 21 | b | 0 | 0 | — | 100 | 100 |
| 22 | b | 0 | 85 | — | 100 | 100 |
| 23 | b | 0 | 0 | — | 90 | 100 |
| 24 | b | 0 | 0 | — | 100 | 100 |
| 25 | b | 60 | 40 | — | 100 | 100 |
| 26 | b | 0 | 0 | — | 90 | 80 |
| 27 | b | 0 | — | — | 80 | 100 |
| 28 | b | 70 | 0 | — | 100 | 100 |
| 29 | b | 0 | 0 | — | 90 | 70 |
| 30 | b | 100 | 0 | — | 90 | 60 |
| 31 | b | 50 | 50 | — | 90 | 90 |
| 32 | b | 0 | 0 | — | 100 | 70 |
| 33 | b | 0 | 0 | — | 100 | 100 |
| 34 | b | 80 | 0 | — | 100 | 100 |
| 35 | b | 0 | 0 | — | 60 | 0 |
| 36 | b | 0 | 0 | — | 50 | 100 |
| 37 | b | 0 | 0 | — | 100 | 100 |
| 38 | b | 0 | 0 | — | 100 | 100 |
| 39 | b | 0 | 50 | — | 95 | 95 |
| 40 | b | 50 | 0 | — | 95 | — |
| 41 | b | 0 | 0 | — | 95 | 50 |
| 42 | b | 0 | 0 | — | 95 | 99 |
| 43 | b | 50 | 95 | 95 | 100 | — |
| 44 | b | 0 | 0 | 95 | 95 | 50 |
| 45 | b | 0 | 0 | — | 95 | 99 |
| 46 | b | 0 | 0 | — | 50 | 95 |
| 47 | b | 80 | 0 | 75 | 100 | — |
| 48 | a | 90 | 0 | 50 | 95 | — |
| 49 | a | 50 | 0 | 50 | 95 | — |
| 50 | a | 90 | 0 | 0 | 75 | — |
| 51 | a | 80 | 0 | 0 | 99 | — |
| 52 | a | 80 | 0 | 0 | 50 | — |
| 53 | a | 0 | 0 | 50 | 85 | — |
| 54 | a | 80 | 0 | 50 | 95 | — |
| 55 | a | 90 | 0 | 50 | 95 | — |
| 56 | a | 90 | 0 | 75 | 100 | — |
| 57 | a | 100 | 0 | 0 | 99 | — |
| 58 | a | 80 | 0 | 0 | 99 | — |
| 59 | a | 0 | 0 | 0 | 99 | — |
| 60 | a | 50 | 0 | 95 | 99 | — |
| 61 | a | 0 | 0 | 0 | 85 | — |
| 62 | a | — | 0 | 85 | 95 | — |
| 63 | a | 0 | 0 | 0 | 100 | — |
| 64 | c | 0 | 0 | — | 98 | 80 |
| 65 | c | 0 | 0 | — | 99 | 85 |
| 66 | c | 0 | 0 | — | 90 | 0 |
| 67 | c | 30 | 0 | — | 90 | 0 |
| 68 | a | 0 | 0 | 50 | 85 | — |
| 69 | a | 50 | 0 | 50 | 85 | — |
| 70 | a | 0 | 0 | 0 | 85 | — |
| 71 | a | 0 | 0 | 0 | 95 | — |
| 72 | a | 0 | 0 | 0 | 95 | — |
| 73 | a | 50 | 0 | 0 | 99 | — |

TABLE 4-continued

Fungicidal Efficacy of Compounds of the Invention.

| Ex. No. | Rate[1] | RB[2] | RSB[3] | WLR[4] | WPM[5] | WSR[6] |
|---|---|---|---|---|---|---|
| 74 | a | 0 | 0 | 50 | 85 | — |
| 75 | a | 0 | 0 | 85 | 75 | — |
| 76 | b | 0 | 0 | 80 | 75 | — |

[1]Test rate: a = 100 PPM; b = 200 PPM; c = 300 PPM; d = 600 PPM
[2]rice blast (*Piricularia oryzae*)
[3]rice sheath blight (*Pellicularia filamentosa* f. sp. *sasiki*)
[4]wheat leaf rust (*Puccinia recondita* (f. sp. *tritici* Races PKB and PLD))
[5]wheat powdery mildew (*Erysiphi graminis* f. sp. *tritici*)
[6]wheat stem rust (*Puccinia graminis* f. sp. *tritici*)
[7]— means not tested

We claim:

1. A compound of the formula:

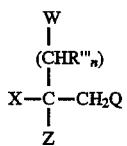

wherein

X is $(C_6-C_{10})$ aryl or $(C_6-C_{10})$aryl substituted with one, two or three substituents selected from the group consisting of hydroxy, halo, acetoxy, trihalomethyl, $(C_1-C_4)$alkyl, $(C_1-C_4)$alkoxy, $(C_1-C_4)$alkylthio, $(C_1-C_4)$alkylsulfinyl, $(C_1-C_4)$ alkylsulfonyl, $(C_1-C_4)$ alkoxy$(C_1-C_4)$alkoxy, $(C_1-C_4)$alkylcarbonyl, $(C_2-C_8)$ alkenyl, $(C_2-C_4)$alkenyloxy, $(C_2-C_8)$ alkenyl, $(C_2-C_4)$ alkenyloxy, $(C_2-C_8)$alkynyl, $(C_2-C_8)$alkenyloxy, phenyl, phenyl monosubstituted with halo, $(C_1-C_4)$ alkyl or $(C_1-C_4)$alkoxy Q is unsubstituted or substituted 1-(1,2,4-triazolyl) or 4-(1,2,4-triazolyl);

Z is $(C_1-C_{12})$alkyl, halo$(C_1-C_{12})$alkyl, $(C_2-C_8)$alkenyl. halo$(C_2-C_8)$alkenyl, $(C_2-C_8)$alkynyl, $(C_3-C_8)$ cycloalkyl, $(C_5-C_8)$cycloalkenyl. cycloalkylalkyl, aryl, aralkyl;

W is —OR, —OCOY, —OCOR'Y, —OR'OR, —NHCOR, -NHCOR'Y, —NHCOY. —OCONHY, wherein A is $(C_1-C_6)$alkyl;

R is Y-alkyl, which is substituted or unsubstituted with 1,2 or 3 or hydrogen, provided that when Z is methyl, R is not haloalkyl;

R' is (—CH(CH$_3$)—)p(—CH$_3$—)$_m$ or (—CH$_2$—)sCH=CH(—CH$_2$—)t;

m is an integer from 0 to 6;

p is 0 or 1, provided m and p are not both 0;

s and t are each independently integers of from 0 to 3:

R''' is phenyl, $(C_1-C_6)$alkyl, $(C_2-C_4)$alkenyl or $(C_1-C_2)$-trialkylsilyl, $(C_1-C_4)$alkyl, all Unsubstituted or substituted with 1,2 or 3 halogens, hydrogen or $(C_1-C_6)$alkyl;

n is an integer from 1 to 6; and

Y is piperidinyl, triazolyl, pyrazinyl, pyrimidinyl, phthalimido, morpholinyl, pyridyl, all substituted or unsubstituted; or the agronomically acceptable enantiomorphs, acid addition salts or metal salt complexes thereof.

2. The compound of claim 1 in which Z is selected from $C_1-C_8$alkyl, $(C_5-C_7)$cycloalkyl, phenyl, benzyl or phenthyl, or phenyl, benzyl or phenethyl the aromatic ring being substituted with up to two halo substituents; R''' is H and n is 1 provided that when Z is methyl, R is not haloalkyl and Z is 1-(1,2,4-triazoyl).

3. The compound of claim 2 in which X is phenyl, or phenyl substituted with chloro, hydroxy, acetoxy, methoxy; Z is is (C1–C6)alkyl, (C5–C6)cycloalkyl, phenyl, benzyl, or phenethyl, or monochloro substituted phenyl, benzyl, or phenethyl provided that when X is phenyl, R is not haloalkyl and Z is 1-(1,2,4-triazoylyl).

4. The compound of claim 3 in which X is phenyl, or phenyl sustituted with chloro, hydroxy, acetoxy, methoxy, or ethoxy, and Z is ethyl, n-butyl, benzyl, 2-chlorobenzyl, or 4-chlorobenzyl.

5. A fungicidal composition which comprises an agronomically acceptable carrier and a fungicidally effective amount of a compound of claim 1.

6. A fungicidal composition which comprises an agronomically acceptable carrier and a fungicidally effective amount of a compound of claim 2.

7. A fungicidal composition which comprises an agronomically acceptable carrier and a fungicidally effective amount of a compound of claim 3.

8. A fungicidal composition which comprises an agronomically acceptable carrier and a fungicidally effective amount of a compound of claim 4.

9. A method for controlling fungi which comprises applying to the locus where control is desired a fungicidally effective amount of a compound of claim 1.

10. A method for controlling fungi which comprises applying to the locus where control is desired or fungicidally effective amount of the compound of claim 2.

11. A method for controlling fungi which comprises applying to the locus where control is desired or fungicidally effective amount of the compound of claim 3.

12. A method for controlling fungi which comprises applying to the locus where control is desired or fungicidally effective amount of the compound of claim 4.

* * * * *